United States Patent
Kochel et al.

(10) Patent No.: US 9,005,633 B2
(45) Date of Patent: Apr. 14, 2015

(54) PSORALEN-INACTIVATED VIRAL VACCINE AND METHOD OF PREPARATION

(75) Inventors: Tadeusz J. Kochel, Frederick, MD (US); Ryan C. Maves, Chula Vista, CA (US); Kevin Porter, Boyds, MD (US)

(73) Assignee: The United States of America as Represented by the Secretary of the Navy., Washington, DC (US)

( * ) Notice: Subject to any disclaimer, the term of this patent is extended or adjusted under 35 U.S.C. 154(b) by 148 days.

(21) Appl. No.: 12/838,449

(22) Filed: Jul. 17, 2010

(65) Prior Publication Data

US 2011/0014233 A1 Jan. 20, 2011

Related U.S. Application Data

(60) Provisional application No. 61/226,395, filed on Jul. 17, 2009.

(51) Int. Cl.
*A61K 39/12* (2006.01)
*C12N 7/06* (2006.01)
*C12N 7/00* (2006.01)
*A61K 39/00* (2006.01)

(52) U.S. Cl.
CPC . *A61K 39/12* (2013.01); *C12N 7/06* (2013.01); *A61K 39/00* (2013.01); *A61K 2039/5252* (2013.01); *C12N 7/00* (2013.01); *C12N 2770/24134* (2013.01); *C12N 2770/24163* (2013.01); *C12N 2770/36163* (2013.01)

(58) Field of Classification Search
None
See application file for complete search history.

(56) References Cited

U.S. PATENT DOCUMENTS

| | | | |
|---|---|---|---|
| 4,124,598 | A | 11/1978 | Hearst et al. |
| 4,169,204 | A | 9/1979 | Hearst et al. |
| 4,196,281 | A | 4/1980 | Hearst et al. |
| 4,693,981 | A | 9/1987 | Wiesehahn et al. |
| 6,455,286 | B1 * | 9/2002 | Wollowitz et al. ......... 435/173.3 |

OTHER PUBLICATIONS

Whitehorn et al., Vaccine, 2011, 29:7221-7228.*
Mayes et al., Vaccine, 2011, 29:2691-2696.*

* cited by examiner

*Primary Examiner* — Stacy B Chen
(74) *Attorney, Agent, or Firm* — Ning Yang; Albert M. Churilla

(57) ABSTRACT

A method to prepare inactivate viral vaccine by exposing the virus to a predetermined concentration of an inactivating psoralen, and a preselected intensity of ultraviolet radiation for a time period sufficiently long to render the virus non-infectious but less than that which would result in degradation of its antigenic characteristics.

15 Claims, 8 Drawing Sheets

PSORALEN-INACTIVATED VIRAL VACCINE AND METHOD OF PREPARATION

CROSS-REFERENCE TO RELATED APPLICATIONS

Figure 1A:
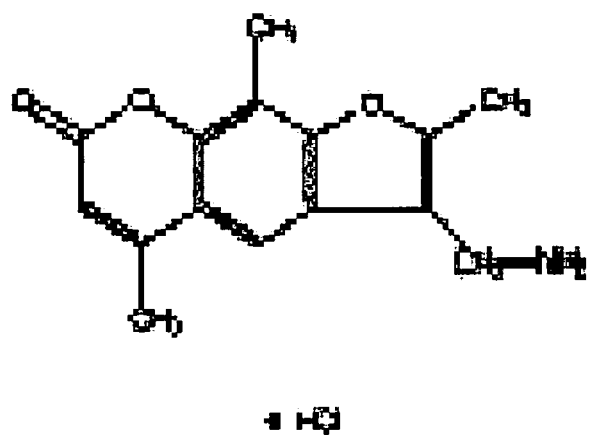
Figure 1A:

This application claims priority to U.S. Provisional application 61/226,395 filed Jul. 17, 2009.

BACKGROUND

The present invention relates to an inactivated viral vaccine. More specifically, the invention relates to a method for preparing dengue virus vaccine using psoralen inactivated viral particles.

Dengue viruses consist of four distinct but closely related single-stranded, enveloped RNA viruses of the genus *Flaviviridae*. Geographically widespread in tropical and subtropical regions, dengue viruses are transmitted to humans primarily through the bite of the *Aedes aegypti* mosquito. Between 50-100 millions human infections occur annually due to dengue, making it the world's most widespread arboviral disease. Clinical manifestations vary among hosts, with presentations that include asymptomatic infections, nonspecific febrile syndromes, the more severe (classic) dengue fever, and finally the life-threatening dengue hemorrhagic fever (DHF) and dengue shock syndrome (DSS). There are an estimated 250,000 cases per year of DHF and DSS worldwide. Most affected patients are young children, who also make up the majority of the approximately 25,000 estimated annual deaths due to dengue infection[1].

Therapeutic options for dengue infection currently are limited to supportive care. No specific therapy for dengue fever exists, although treatment such as aggressive fluid management with crystalloid solutions has been shown to be effective[2]. However, immunomodulation with corticosteroids[3] or intravenous immunoglobulin[4] has not demonstrated any benefit in human trials.

Primary dengue infection leads to short-lived heterologous immunity to all four dengue serotypes[5]. However, lasting immunity persists only to the infecting serotype, leaving previously-infected persons susceptible to the other three serotypes of the virus. Many endemic regions of the world have multiple circulating serotypes at any given time, limiting the protection gained from a prior infection. Furthermore, prior dengue infection is a major risk factor for the subsequent development of DHF and DSS following re-infection with a heterotypic dengue serotype. Although the molecular and immunologic mechanisms for DHF are not completely understood, it is believed that antibodies to the primary infecting serotype interact with the envelope (E) protein on the surface of a heterotypic dengue serotype, which leads to an increased uptake of virus into susceptible host cells through an immunoglobulin constant chain receptor (FcR)-dependent mechanism[6]. These infected cells permit dengue virus to replicate in greater quantities, causing increased viremia and disease severity. Homotypic antibodies to the infecting serotype plays a major role in the prevention of recurrent infection, although it is uncertain to what extent humoral factors are responsible for this immunity as compared with cell-mediated immunity[30,31]. Heterotypic antibodies to a prior infecting dengue serotype appear to contribute to the subsequent development of DHF, with these heterotypic antibodies enhancing the ability of dengue viruses to infect cells via binding to the immunoglobulin FcR[32,33]. Additionally, low-affinity cell-mediated responses to dengue re-infection may also lead to excessive cytokine release, contributing to the vascular leak that is the hallmark of DHF[7].

As a result, dengue vaccine development has been hindered by the competing interests to develop a vaccine that provides lasting and uniform protection against all four dengue serotypes, and the need to avoid predisposing the vaccine recipients to an increased risk of DHF and DSS. Vaccine candidates currently in development include a recombinant live-attenuated viral vaccine, DNA vaccines encoding for dengue viral epitopes, and a vaccine using a recombinant YF17D (vaccine strain) yellow fever virus with a modified genome that encodes for dengue-specific antigen[8]. Phase 1 and 2 human trials have been completed for some of these candidates[9,10,11,12], but none is presently ready for commercial release. These products show promise but may require boosting, either with multiple vaccine doses or with a separate agent.

A successful dengue vaccine will need to produce high-affinity and enduring antibodies to all four serotypes, possibly by means of periodic booster doses. There are promising vaccine candidates that utilize individual dengue epitopes (such as domain III of the dengue envelope (E) protein). An inactivated viral vaccine, by contrast, has the potential to present these epitopes to the host immune system in their native confirmation. In addition, cell-mediated immunity is generally lacking from inactivated vaccines due to the absence of viral replication. The exact contribution of cell-mediated immunity to the development of severe dengue is unclear. T-lymphocytes may assist with containment of recurrent homotypic infections through the elimination of excess virus not controlled adequately by antibody, but there is evidence that low-affinity T-cell responses to heterotypic infection contributes to DHF by excessive cytokine production (such as TNF-alpha)[30,34,35]. Prior T-cell immunity does not seem to be a necessary step in the pathogenesis of DHF, however, as demonstrated by the occurrence of DHF in infants with residual maternal anti-dengue antibody but no personal history of dengue infection[36]. Therefore, an inactivated vaccine may overcome the problems associated with excessive cytokine release.

Psoralen (also called psoralene) is the parent compound in a family of natural products known as furocoumarins. Psoralens are photoreactive compounds that are freely permeable in phospholipid membranes and intercalate between double-stranded nucleic acids. Following exposure to long wave ultraviolet radiation (UVA) with wavelength of 300-400 nm, the intercalated psoralen covalently crosslink complementary pyrimidine residues, leading to viral inactivation through inhibition of genome replication. Psoralen interaction with viral nucleic acids leaves immunogenic surface epitopes intact[13], raising the possibility that a psoralen-inactivated virus may serve as a vaccine candidate. This photo-crosslinking property of psoralens has been exploited to inactivate microorganisms in the blood supply[14,15], for treatment of skin disorders[16], to inactivate viral pathogens prior to organ transplantation[17], and for inactivation of viruses for potential vaccines[18,19,20].

Psoralen-inactivated viruses should, in theory, retain their three-dimensional structure, permitting the development of antibodies to multiple epitopes that may participate in immunity. Psoralens are freely permeable through lipid bilayers and do not appear to interact with proteins. Additionally, they only induce cross-linking of pyrimidines following UV exposure[24,25]. This feature of psoralens has made them attractive in transfusion medicine for pathogen inactivation, wherein they damage the nucleic acid of pathogenic contaminants without disrupting the donor-derived erythrocytes, platelets, and coagulation factors themselves[14, 15, 26].

Psoralens also have a good safety record in humans. There is increasing experience with the use of psoralens in blood banking, particularly the use of amotosalen as an alternative to traditional leukoreduction methods for the prevention of CMV transmission[14]. The oral and topical use of psoralens in the treatment of psoriasis has been associated with photosensitivity, contact dermatitis, and DNA damage in histologic specimens from treated tissue[27, 28, 29]. These adverse reactions are due in part to the direct exposure of human skin to UVA and psoralen, and do not seem likely to be of concern following vaccine preparation, assuming adequate purification of the inactivated virus preparation. Good safety record and photo-crosslinking property of psoralens lend it to possible use in inactivating virus vaccines.

U.S. Pat. Nos. 4,124,598 and 4,196,281 to Hearst et al. suggest the use of psoralen derivatives to inactivate RNA viruses, but include no discussion of the suitability of using the inactivated viruses for vaccines. U.S. Pat. No. 4,169,204 to Hearst et al. suggest that psoralens may provide a mean for inactivating viruses for the purpose of vaccine production but presents no experimental support for this proposition. European patent application 0 066 886 by Kronenberg teaches the use of psoralen inactivated cells, such as virus-infected mammalian cells, for use as immunological reagents and vaccines. Hanson (1983) reported studies suggesting that oxidative photoreactions between psoralens and proteins may occur[37]. However, it also has been recognized that inactivation of viruses by exposure to ultraviolet radiation in the presence of furocoumarin compounds can degrade the antigenic structure of the viral particles. While such degradation can be limited by employing less rigorous inactivation conditions, certain recalcitrant viruses require relatively harsh inactivation conditions in order to assure that all residual infectivity is eliminated. Thus, the inactivation conditions required to eliminate substantially all infectivity in such recalcitrant viruses can also degrade the viral particle so it is unsuitable for use as the immunogenic substance in a vaccine. Even if the degradation is not so complete, partial degradation of the antigenic characteristics may render the vaccine less effective than would be desirable. That is, the vaccine may require higher concentrations of the inactivated viral particles in each inoculation, and/or the vaccination program may require additional inoculations in order to achieve immunity.

U.S. Pat. No. 4,693,981, by Wiesehahn et al. disclosed an improved method for preparing inactivated viral vaccine without substantially degrading its antigenic characteristics. Wiesehahn et al prepare a selected group of viruses for vaccine uses by exposing the virus to a preselected concentration of an inactivating furocoumarin and a preselected intensity of ultraviolet radiation in the presence of inert gases or oxygen scavengers. However, this method calls for long period (2-60 hours) of high intense UVA exposure (0.1 m W/cm$^2$ to about 5 W/cm$^2$), which must be carried out in absence of oxygen or oxygenized species to preserve the antigenic characteristics of the virus. The absence of oxygen and oxygenized species are maintained through additional processes, such as removing the oxygenized species from the inactivation medium prior to irradiation through flushing with non-oxidizing gas and adding oxygen scavengers to the medium. The patent contains no discussion of the suitability of this method in preparing inactivating dengue viruses or Flaviviridae virus vaccines.

Although psoralen is known to be effective in inactivating viruses, its suitability for preparing an inactivating arboviral vaccine or more specifically a dengue viral vaccine is still unclear. The optimal inactivation conditions for such vaccine preparation, including the length of UVA exposure, the UV intensity, the concentration and selection of psoralen, are left to be experimentally determined, which is the objective of this study.

DETAILED DESCRIPTION OF FIGURES

FIG. 1(a) psoralen compounds tested for dengue-1 virus (DENV-1) inactivation: 4'-Aminomethyltrioxsalen hydrochloride (AMT). SIGMA: Product Number A 4330, CAS RN: 62442-61-9. Synonyms: 4'-Aminomethyl-4,5,8-trimethylpsoralen hydrochloride; 4'-Aminomethyl-4,5',8-trimethylpsoralen hydrochloride; 3-Aminomethyl-2,5,9-trimethyl-7Hfuro[3,2g][1]benzopyran-7-one hydrochloride. Molecular formula: C15H15NO3.HCl. Formula weight: 293.75.

Figure 1B:
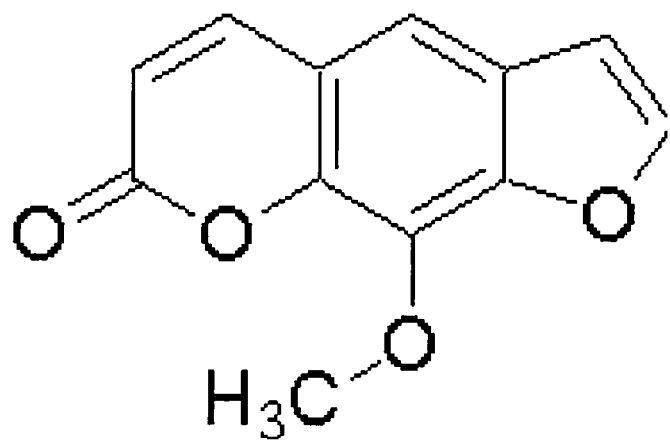

FIG. 1(b) psoralen compounds tested for DENV-1 inactivation: 8-Methoxypsoralen (8-MOP). ACROS COM Cat. 214150010, CAS RN: 298-81-7. Synonyms: Methoxsalen, Xanthotoxin, Ammoidin. Molecular formula: C12H8O4. Formula weight: 216.19

Figure 1C:
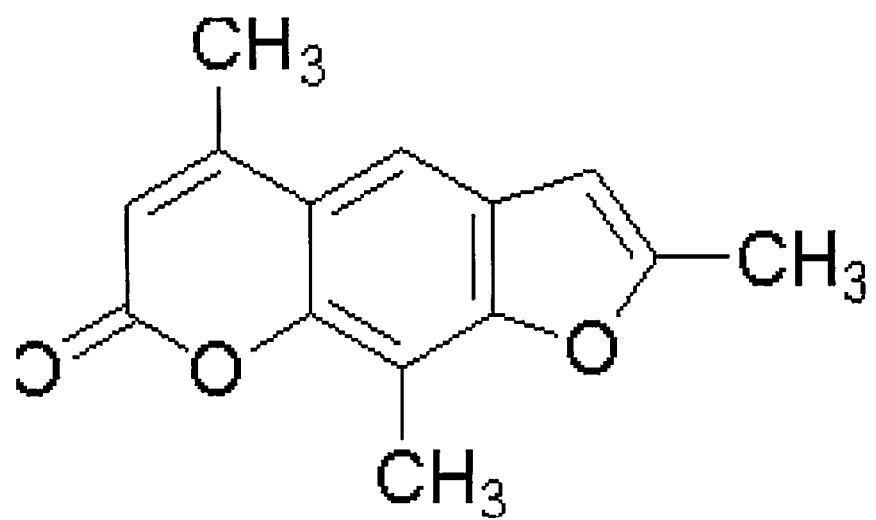

FIG. 1(c) psoralen compounds tested for DENV-1 inactivation: 4,5',8-Trimethylpsoralen (TMP). ACROS COM Cat 229881000, CAS RN: 3902-71-4. Synonyms: Trioxalen, 2,5,9-Trimethylfuro[3,2-g]benzopyran-7-one. Molecular formula: C14H12O3. Formula weight: 228.24.

FIG. 2(a) detectable IgG following challenge with DENV-1 in *Aotus nancymae* monkeys.

FIG. 2(b) detectable IgM following challenge with DENV-1 in *Aotus nancymae* monkeys.

Figure 3A:
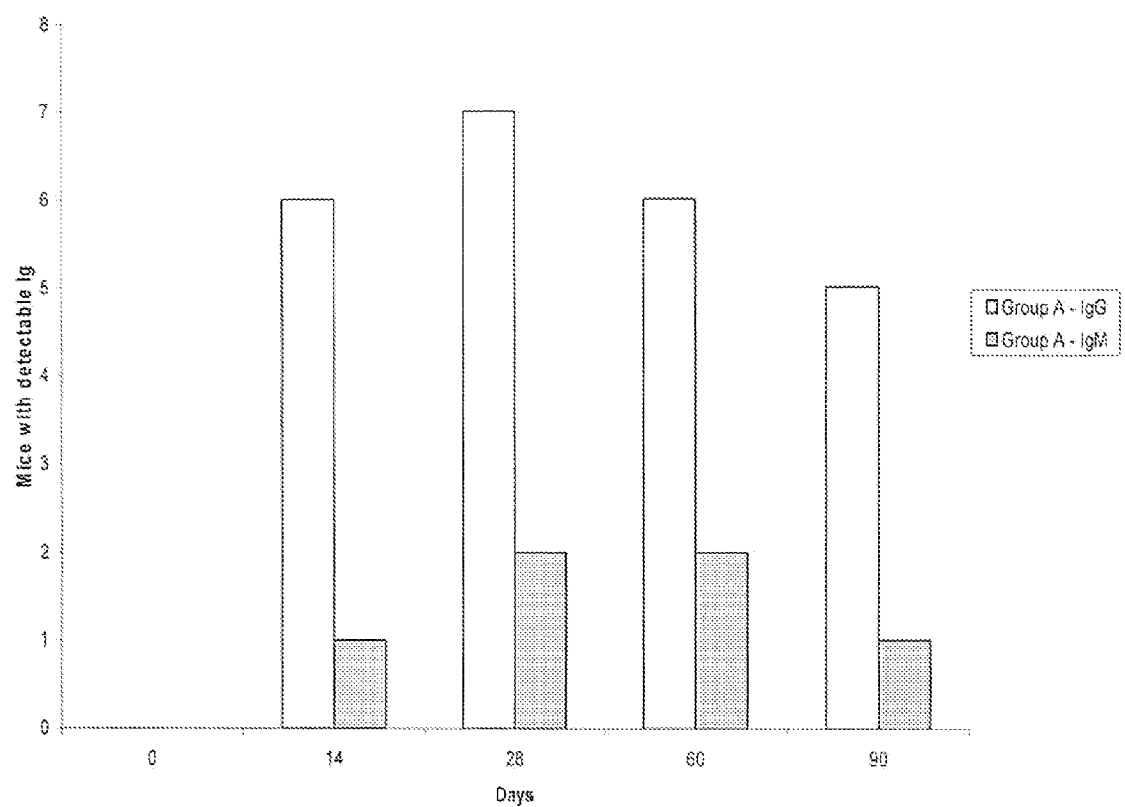

FIG. 3(a) Immunogenicity of 5 ng vaccine candidate dose (group A).

Figure 3B:
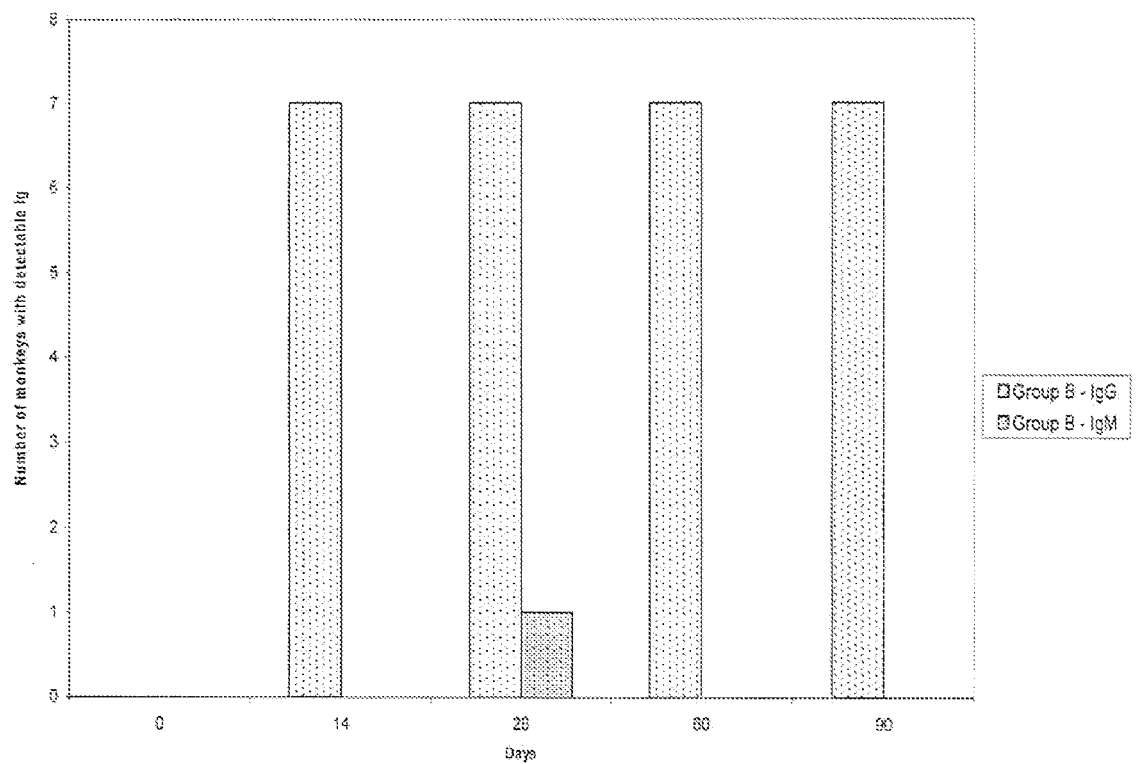

FIG. 3(b) Immunogenicity of 10 ng vaccine candidate dose (Group B).

Figure 3C:
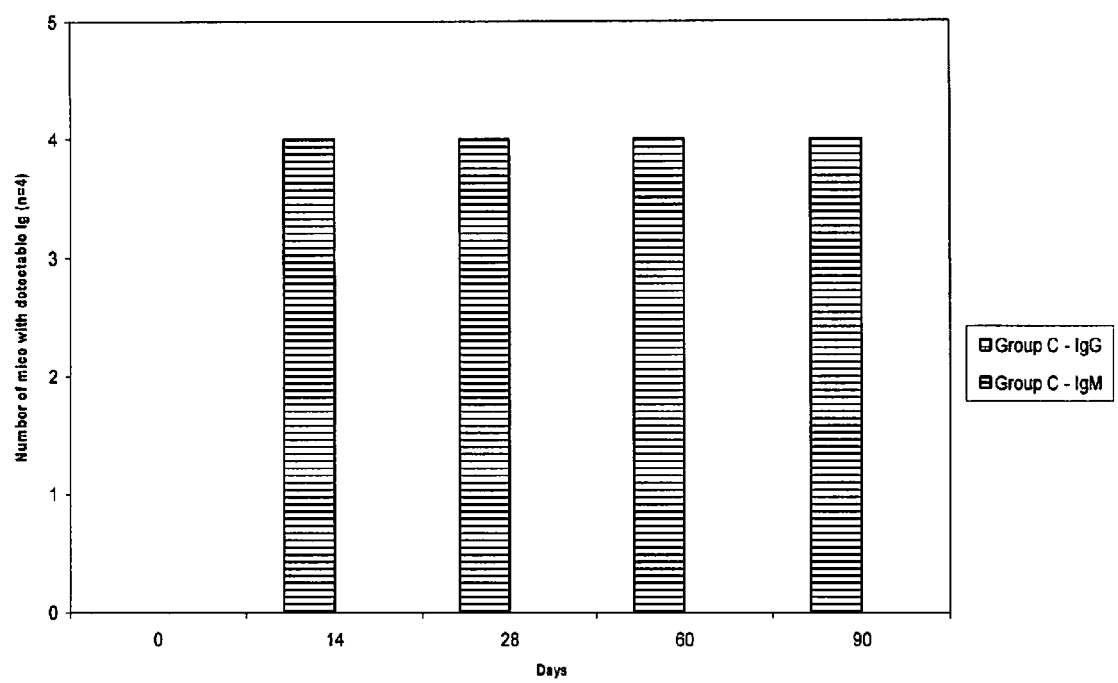

FIG. 3(c) Immunogenicity of 10 ng vaccine candidate dose (Group c).

Figure 4:
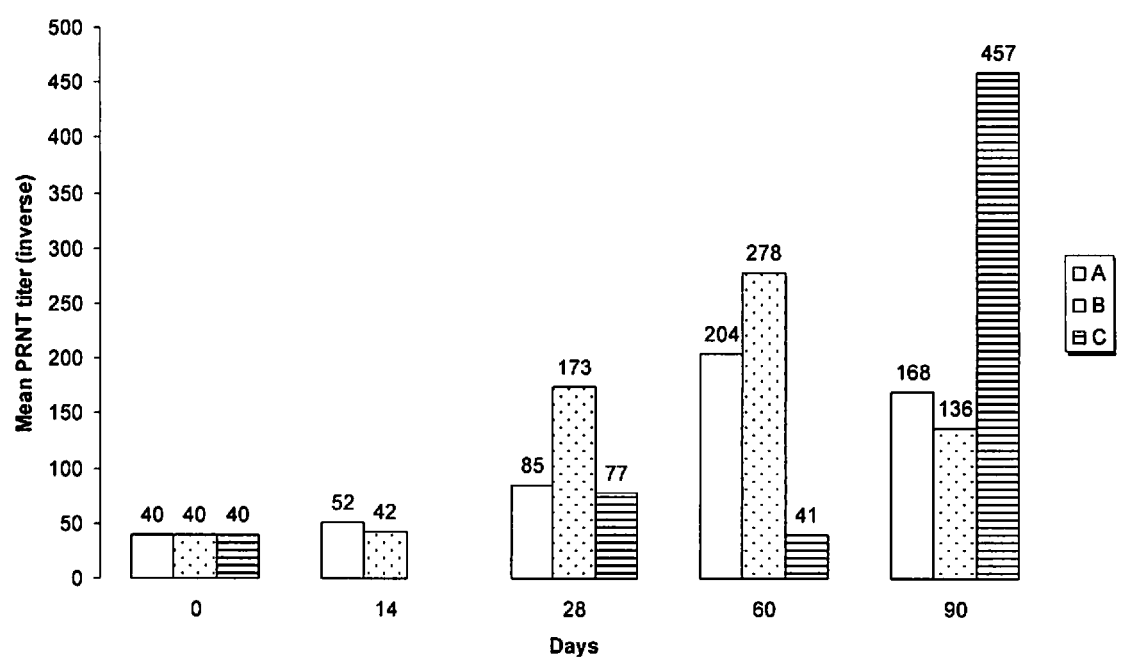

FIG. 4 Geometric mean of PRNT titers.

SUMMARY OF THE INVENTION

According to the present invention, dengue viral vaccines are prepared by inactivating dengue virus through treatment with a psoralen, followed by sufficient exposure to an ultraviolet (UVA) light of predetermined wavelength. The inactivation need not be carried out in absence of oxygen oxidizing species. The prepared vaccine comprises inactivated dengue virus of one or more of the four dengue serotypes. The condition for inactivation allows for inactivation of dengue virus without loss of immunogenicity. The method of preparation according to the present invention may also be used to prepare vaccines against other Arboviral infections, including but not limited to infections caused by Yellow Fever (YF), West Nile Virus (WNV), Saint Louis Encephalitis (SLE) and Venezuelan Equine Encephalitis (VEE) viruses.

DETAILED DESCRIPTION OF THE INVENTION

According to the present invention, vaccines useful for the inoculation of mammalian hosts, including both animals and humans, against infection by dengue virus are provided. The vaccines are prepared by inactivation of live dengue virus in a medium containing an amount of an inactivating psoralen sufficient to inactivate the virus upon subsequent irradiation with ultraviolet radiation of predetermined intensity (UVA). Degradation of the antigenic characteristics of the live virus is reduced or eliminated by carefully selecting psoralen(s) of a pre-determined concentration and exposing the virus to only minimum intensity and duration of UVA necessary to inactivate the virus.

Suitable vaccines may be prepared by combining the inactivated virus with a physiologically-acceptable carrier, typically an adjuvant, in an appropriate amount to elicit an immune response, e.g., the production of serum neutralizing antibodies, upon subsequent inoculation of the host.

The present invention is suitable for producing vaccines against one or all four serotypes of dengue virus as well as other Arbovirus. The vaccine may comprise inactivated dengue virus from one or more serotypes. The inactivation of each serotype of dengue virus may be carried out individually, and subsequently combined in the final vaccine or carried out together in a single process.

In preparing the present vaccines, sufficient amounts of the virus to be inactivated may be obtained by growing seed virus in a suitable mammalian cell culture. Seed virus, in turn, may be obtained by isolation from an infected host. Suitable mammalian cell cultures include primary or secondary cultures derived from mammalian tissues or established cell lines such as Vero cells, monkey kidney cells, BHK21 hampster cells, LMTK31 cells, and other cells permissive for the desired virus, and which may be grown in vitro as monolayer or suspension cultures. The cell cultures are grown to approximately 80% saturation density, and infected with the virus at a low multiplicity of infection (MOI), usually between about 0.05 and 0.005, preferably at about 0.01. After adsorbing the viral inoculum to the cells by incubation for a limited period of time at a temperature in the range from 35° C. to 40° C., an appropriate growth or maintenance medium is added. The cells are further incubated at about the same temperature, in the presence of about 5% carbon dioxide in air, until a sufficient amount of virus has been produced.

The growth and maintenance medium is conventional mammalian cell culture medium, such as Eagle's Minimum Essential Medium or Medium 199, usually supplemented with additives such as broth prepared from dehydrated standard microbial culture media, fetal bovine serum, fetal calf serum, or the like.

Psoralens may be used in the inactivation process include psoralen and substituted psoralens, in which the substituent may be alkyl, particularly having from one to three carbon atoms, e.g., methyl; alkoxy, particularly having from one to three carbon atoms, e.g., methoxy; and substituted alkyl having from one to six, more usually from one to three carbon atoms and from one to two heteroatoms, which may be oxy, particularly hydroxy or alkoxy having from one to three carbon atoms, e.g., hydroxy methyl and methoxy methyl, or amino, including mono- and dialkyl amino or aminoalkyl, having a total of from zero to six carbon atoms, e.g., aminomethyl. There will be from 1 to 5, usually from 2 to 4 substituent, which will normally be at the 4, 5, 8, 4' and 5' positions, particularly at the 4' position. Illustrative compounds include 5-methoxypsoralen; 8-methoxypsoralen (8-MOP); 4,5',8-trimethylpsoralen (TMP); 4'-hydroxymethyl-4,5',8-trimethylpsoralen (HMT); 4'-aminomethyl-4,5',8-trime-thylpsoralen (AMT); 4-methylpsoralen; 4,4'-dimethylpsoralen; 4,5'-dimethylpsoralen; 4',8-dimethylpsoralen; and 4'-methoxymethyl-4,5',8-trimethylpsoralen. Of particular interest are AMT4,5', TMP and 8-MOP.

Different psorlarens may be used individually or in combination in the inactivation process. The psoralens may present in amounts ranging from 1-100 μg/ml, preferably from about 5-25 μg/ml. In carrying out the invention, the psoralen(s) are combined with the viral suspension, conveniently a viral suspension in an aqueous buffered medium, such as those used for storage. The virus concentration is generally about $1\times10^5$ to $1\times10^6$ pfu/ml, and preferably about $3\text{-}5\times10^5$ pfu/ml.

Although viral inactivation according to the present invention will normally be carried out in an inactivation medium as just described, it may be desirable to introduce psorlarens to the virus by addition to a cell culture medium in which the virus is grown. The inactivation is then carried out by separating the live viral particles from the culture medium, and exposing the particles to ultraviolet light in an inactivation medium which may or may not contain additional psoralens.

When employing psoralens with limited aqueous solubility, typically below about 50 g/ml, it has been found useful to add an organic solvent, such as dimethyl sulfoxide (DMSO), ethanol, glycerol, polyethylene glycol (PEG) or polypropylene glycol, to the aqueous treatment solution. For psoralens having limited solubility, such as 8-MOP, TMP, and AMP, adding a small amount of such organic solvents to the aqueous composition, typically in the range from about 1 to 25% by weight, more typically from about 2 to 10% by weight, the solubility of the psoralen can be increased to about 200 ng/ml, or higher. Such increased psoralen concentration may permit the use of shorter irradiation times. Also, inactivation of particularly recalcitrant microorganisms may be facilitated without having to increase the length or intensity of ultraviolet exposure. The addition of an organic solvent may be necessary for inactivation of some viruses with particular furocoumarins. The ability to employ less rigorous inactivation conditions is of great benefit in preserving the antigenicity of the virus during inactivation.

The psoralen may be added to the viral suspension in a single addition or in multiple additions, where the virus is irradiated between additions. The psoralens may also be added continuously during the entire treatment period, or a portion thereof. Usually, the number of additions will be from 1 to 4. The total amount of psoralen is sufficient to provide a concentration between 1 ng/ml and 100 ng/ml.

The time of UV irradiation will vary depending upon the light intensity, the concentration of the psoralen, the concentration of the virus, and the manner of irradiation of the virus receives, where the intensity of the irradiation may vary in the medium. The time of irradiation will be inversely proportional to the light intensity. The total time will usually be at least about 5 minutes and no more than about 30 minutes, generally ranging from about 5 to 10 minutes.

The light, which is employed, will generally have a wavelength in the range from about 300 nm to 400 nm. Usually, an ultraviolet light source will be employed together with a filter for removing UVB light. The intensity will generally range from about 150 μW/cm2 to about 1500 μW/cm2, although in some cases, it may be higher.

Prior to treatment with ultraviolet light, the virus furocoumarin solution is placed upon a bed of ice. The temperature for the irradiation is preferably under 25° C. During irradiation, the medium may be maintained still, stirred or circulated. The solution may be either continuously irradiated or be subjected to alternating periods of irradiation and non-irradiation. The circulation may be in a closed loop system or in a single pass system ensuring that the entire sample has been exposed to irradiation.

It may be desirable to remove the unexpended psoralen and/or its photobreakdown products from the irradiation mixture. This can be readily accomplished by one of several standard laboratory procedures such as dialysis across an appropriately sized membrane or through an appropriately sized hollow fiber system after completion of the irradiation. Alternatively, one could use affinity methods for one or more of the low molecular weight materials to be removed.

The inactivated virus may then be formulated in a variety of ways for use as a vaccine. The concentration of the virus will generally be from about $1 \times 10^5$ to $1 \times 10^6$ pfu/ml, and preferably about $3-5 \times 10^5$ pfu/ml, as determined prior to inactivation.

EXAMPLE 1

Psoralen and Virus Selection

Three psoralen compounds with differing solubility and intercalation properties were selected for viral inactivation testing: 4'-aminomethyltrioxsalen hydrochloride (AMT) (Sigma-Aldrich, product number A4330, CAS number 62442-61-9); 8-methoxypsoralen (8-MOP) (Acros Organics, catalog number 214150010, CAS number 298-81-7); and 4,5',8-trimethylpsoralen (TMP) (Acros Organics, catalog number 229881000, CAS number 3902-71-4).

DENV-1 (Dengue virus serotype 1) Western Pacific 74 strain was selected as the virus for this study. This virus has been used in prior vaccine efforts[21, 22] and was propagated in *Aedes albopticus* C6/36 clonal cell culture.

5 ml aliquots of DENV-1 viral culture supernatant at a concentration of $3.4 \times 10^5$ plaque-forming units (PFU)/ml were transferred into 60×15 mm Petri dishes. Four test groups of dishes were made. A single psoralen compound (either AMT, 8-MOP, or TMP) was added to each dish in the first three groups, while the fourth group had no psoralen added and served as control. Dishes were exposed to UVA radiation at 365 nm (UVAB-18 lamp, UltraLum, Inc., Claremont, Calif.) for 0, 1, 5, 10, or 20 minutes at an intensity of 200 or 1000 µW/cm². Specimens were then re-titered in BHK cell culture to assess for plaque formation.

Results

Table 1 shows the summary of vaccine candidate selection results. AMT, 8-MOP, and TMP were added to DENV-1 and exposed to UVA radiation. Control specimens exposed to no UVA light produced a titer of $5.63 \times 10^5$ PFU/ml. No detectable PFUs were noted following 10 minutes of 200 µW/cm2 of UVA to AMT-containing DENV-1 supernatant as well as following 5 minutes of exposure to 1000 µW/cm2. The former was chosen as the candidate for in vitro testing based on its lower overall energy exposure.

EXAMPLE 2

In Vitro Viral Inactivation Using Mouse Sera

Vaccine Candidate Preparation

Once an effective psoralen/UVA dose combination was identified, the inactivated virus was purified using a Centrisep columns (Princeton Separation, catalog #CS-901, Adelphi, N.J.). 10 mM of phosphate-buffered saline (PBS) and 10% aluminum hydroxide gel (Alhydrogel) (Sigma, Product number A 8222) were added to purified inactivated virus, with a final equivalent inactivated DENV-1 concentration of $3 \times 10^5$ PFU/ml (10 ng).

Mouse Inoculation and Blood Sampling

Three groups of seven study-naïve, adult Swiss-Webster outbred (CFW) *Mus musculus* mice were selected from the Naval Medical Center Detachment (NMRCD) mouse colony. No mice possessed anti-dengue antibody at baseline as determined by enzyme-linked immunoassay (EIA), and all were 300 g or greater in mass. All procedures were conducted in accordance with protocols approved by the NMRCD Institutional Animal Care and Use Committee. All mice were euthanized humanely at the conclusion of the experiment. All injections and blood sampling were performed by trained personnel using ketamine (100 mg/ml)/acepromazine (5 mg/ml)/xylazine (20 mg/ml) as an intraperitoneal injection administered at a starting dose of 0.1 ml/100 g body mass and titrated to effect.

Group A received 0.05 ml of vaccine candidate (5 ng) injected intradermally into the tail on days 0, 14, and 28. Group B received 0.1 ml of vaccine candidate (10 ng) injected on the same days. Group C received control injections of 10% Alhydrogel and PBS. Blood samples were obtained under anesthesia from the retro-orbital sinus of the mice on days 0, 14, 28, 59, and 90.

EIA for Detection of Anti-DENV-1 IgM and IgG in Mouse Sera

A capture EIA was standardized in order to detect anti-DENV-1 IgM in mice. 96-well format plates were coated overnight at 4° C. with goat anti-mouse IgM. At the end of incubation and after plate washing, mouse sera diluted to 1/100 were added to the plates and incubated for one hour at 37° C. Afterwards, DENV-1 WestPac 74 antigen derived from inactivated whole virus was added and again incubated for one hour at 37° C. Next, rabbit hyperimmune sera with anti-DENV specificity and anti-rabbit peroxidase conjugate were added and incubated for one more hour at 37° C. The plates were washed after incubation time. Finally, ABTS substrate (KPL, Inc., catalog number 50-62-01, Gaithersburg, Md.,

TABLE 1

Psoralen inactivation of dengue virus

| UV Time (Min) | 4'-Aminomethyltrioxalen hydrochloride (AMT) | | 8-Methoxypsoralen (8-MOP) | | 4,5',8-Trimethylpsoralen (TMP) | | No Psoralen | |
|---|---|---|---|---|---|---|---|---|
| | UV-A 1000 uW/cm² | UV-A 200 uW/cm² | UV-A 1000 uW/cm² | UV-A 200 uW/cm² | UV-A 1000 uW/cm² | UV-A 200 uW/cm² | UV-A 1000 uW/cm² | UV-A 200 uW/cm² |
| 0 | $1.92 \times 10^5$ | $1.92 \times 10^5$ | $6.14 \times 10^5$ | $6.14 \times 10^5$ | $4.86 \times 10^5$ | $4.86 \times 10^5$ | $5.63 \times 10^5$ | $5.63 \times 10^5$ |
| 1 | 90 | $4.32 \times 10^4$ | $3.46 \times 10^5$ | $4.35 \times 10^5$ | $1.54 \times 10^5$ | $3.33 \times 10^5$ | $4.90 \times 10^5$ | $3.58 \times 10^5$ |
| 5 | 0 | $1.70 \times 10^2$ | $1.09 \times 10^5$ | $2.94 \times 10^5$ | $4.60 \times 10^3$ | $1.47 \times 10^5$ | $2.05 \times 10^5$ | $3.33 \times 10^5$ |
| 10 | 0 | 0 | $5.12 \times 10^4$ | $2.18 \times 10^5$ | 40 | $8.64 \times 10^4$ | $2.05 \times 10^5$ | $3.33 \times 10^5$ |
| 20 | 0 | 0 | $6.00 \times 10^3$ | $1.66 \times 10^5$ | 0 | $2.24 \times 10^4$ | $1.86 \times 10^5$ | $2.94 \times 10^5$ |

$1-6 \times 10^5$ PFU DENV-1 West Pac 74 was treated with 10 ug/ml psoralen compound and UVA for 0-20 minutes, Centri-sep purified and PFU were determined USA) was added to develop color. After 30 minutes, the plates were read using a spectrophotometer at a wavelength of 405 nm.

To detect anti-DENV-1 IgG, 96-well format plates were coated overnight at 4° C. with DENV-1 antigen. After the plate wash process, mouse sera diluted to 1/100 was added to the plates and incubated for one hour at 37° C., followed by the addition of anti-human IgG conjugate (also incubated for one hour) at 37° C. Finally, ABTS substrate was added for color development. After 30 minutes, the plates were read using a spectrophotometer at a wavelength of 405 nm.

For IgG and IgM EIAs, 0.10 OD was determined as the cut-off value for positive antibody. Adjusted optical density (OD) values were determined by the difference of the OD of the control antigen-coated well subtracted from the corresponding viral antigen-coated well.

Neutralization Tests

Plaque reduction neutralization test (PRNT) assays were performed using BHK-21 cell in 24-well polystyrene plates as described previously[23]. Briefly, serial dilutions (1/40, 1/80, 1/160 and 1/640) of heat-inactivated mouse serum were prepared and mixed with an equal volume of a working dilution of DENV-1 West Pac 74 (10-20 PFU/50 μL) and then incubated at 4° C. overnight. At the end of incubation, the diluted mixture was inoculated into 24-well plates containing $3 \times 10^5$ PFU/ml of a BHK cell suspension. The infected plates were incubated for 3 h at 37° C. under 5% C02 atmosphere. Then the wells were overlaid with a viscous medium that containing carboxymethyl cellulose. Plates were incubated for 7 days at 37° C. under 5% C02 atmosphere. After removal from the incubator, the medium was dumped by inverting plates over a receptacle containing sodium hypochlorite, and plates were rinsed gently under tap water and fixed and stained with 0.5 ml, per well, of a solution that contains naphthol blue-black. The plaques were counted and 50% plaque reduction was determined by Probit analysis.

Results of the Mouse Experiment

Figure 2:
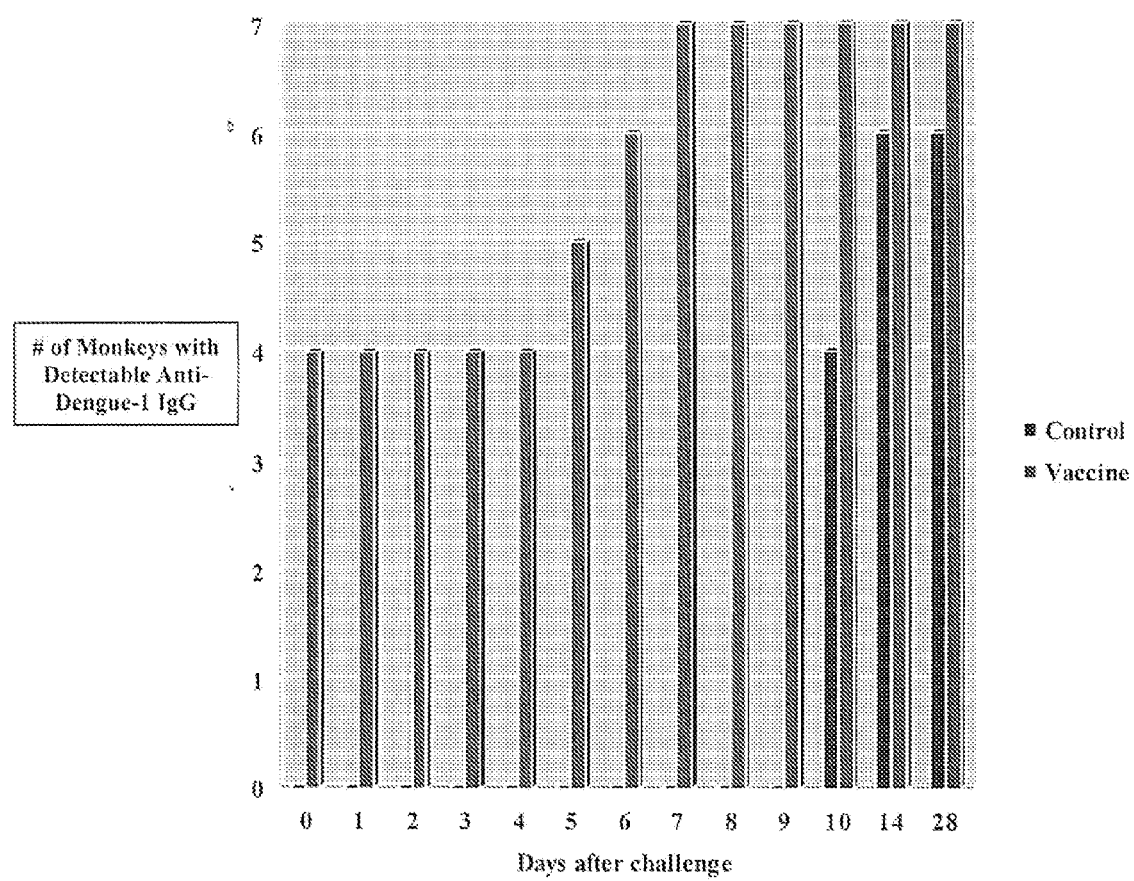
Figure 2:
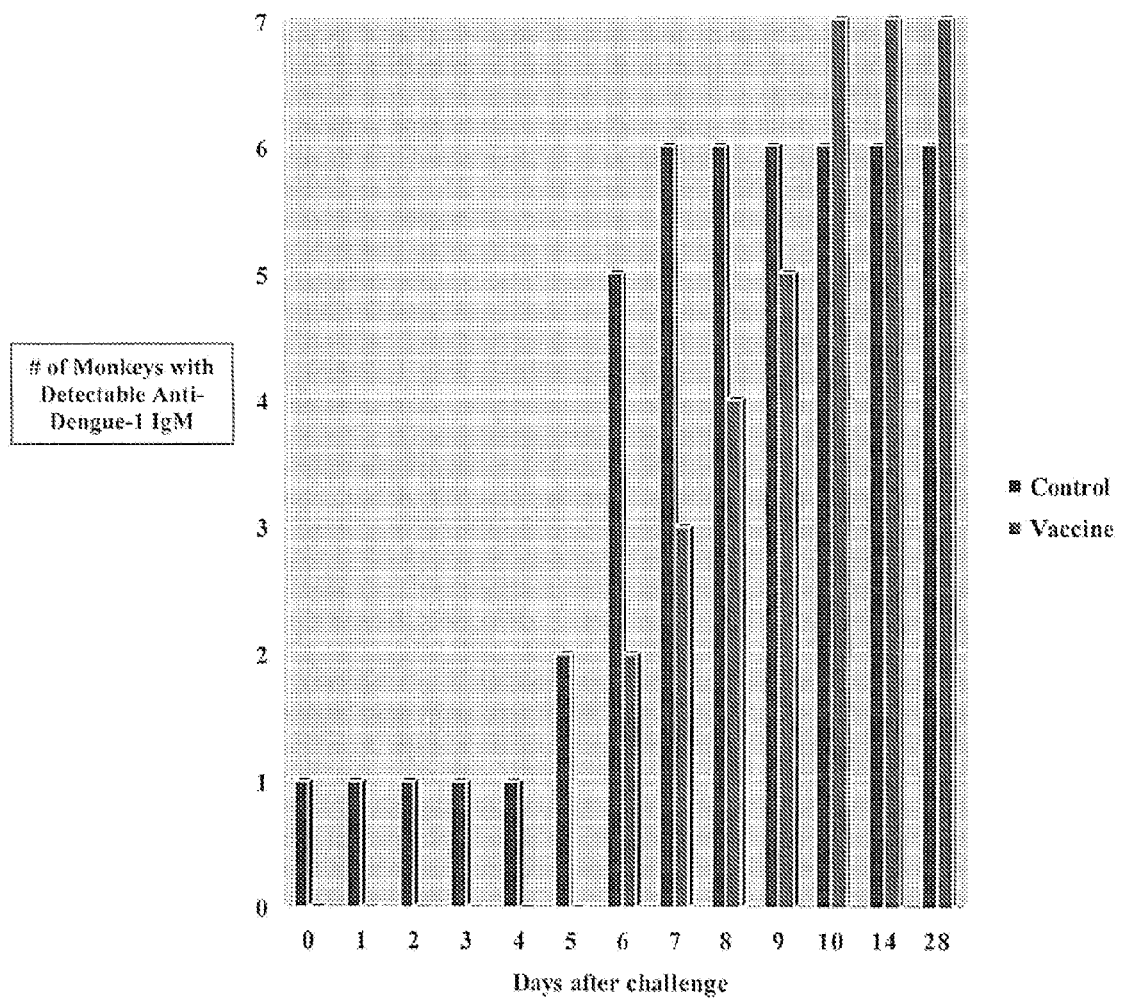

FIG. 2 (a-c) and FIG. 4 show serologic responses in subject mice. All mice were seronegative for anti-DENV-1 antibodies by EIA and $PRNT_{50}$ at baseline. Following the initial vaccine dose at 14 days, mice in group A (low-dose vaccine) had detectable IgG in 6/7; of this group, one mouse additionally had both a positive IgM and $PRNT_{50}$. Group B (high-dose vaccine) mice had detectable IgG in 7/7 and a positive $PRNT_{50}$ in 2/7. Interestingly, no group B mice had detectable IgM.

At day 28 (following 2 vaccine doses), all group A mice had detectable anti-DENV-1 IgG, with 3/7 having a positive $PRNT_{50}$ and 2 of those 3 having detectable IgM. At 59 days (following all 3 vaccine doses), 5/7 mice in group A had positive $PRNT_{50}$, but detectable IgG and IgM declined to 6/7 and 1/7, respectively. At 90 days, one mouse in this group had died; of the remaining 6 mice, 5/6 still had a positive $PRNT_{50}$ although mean titers had declined. 5/6 still had positive IgG and 1/6 a positive IgM, with declining OD measurements as compared with those at 59 days.

7/7 group B mice showed detectable IgG and positive $PRNT_{50}$ at days 28 and 59. Again, the presence of anti-DENV-1 IgM was rare, with a single mouse having showing a detectable IgM by EIA at day 28 only. At day 90, all 7 mice retained a positive IgG, with no detectable IgM. 6/7 retained a positive $PRNT_{50}$ at day 90, with declining mean titers noted but to a lesser magnitude than in group A.

Group C (control) mice received only adjuvant and PBS injections on days 0, 14, and 28. No detectable anti-DENV-1 IgM, IgG, or positive $PRNT_{50}$ assays were noted at days 0, 14, 28, 59, or 90.

Discussion

Based on the above findings, AMT-inactivated DENV-1 is immunogenic in *Mus musculus*, raising the possibility of psoralen/UVA inactivation as a method for dengue vaccine development. Natural infection with dengue viruses produces a lasting sterile immunity to that particular serotype, although not to the others.

Several questions remain following this pilot study. The waning of antibody titers in treated mice over 90 days suggests that this particular formulation, while immunogenic, may benefit from strategies to augment its response (e.g., different adjuvants, higher vaccine doses, or alternate routes of administration). Testing in non-human primates will provide additional data about the necessary vaccine dose and duration of serologic response, as well as immunity following in vivo dengue virus challenge.

EXAMPLE 3

In Vivo Immunogenicity Testing of Psoralen-Inactivated Dengue-1 Virus Vaccine Candidate in *Aotus nancymaae* Monkeys Psoralen Selection and Vaccine Candidate Preparation In a previous experiment, it is demonstrated that DENV-1 can be deactivated using 10 μg/ml of 4-aminomethyltroxsalen (AMT) with 10 minutes of exposure to UVA at a dose of 200 μW/cm2. 10 mM of phosphate-buffered saline (PBS) and 10% aluminum hydroxide gel (Alhydrogel) were added to purified inactivated virus, with a final equivalent inactivated DENV-1 concentration of $3 \times 10^5$ PFU/ml (10 ng).

Administration of Vaccine Candidate

Two groups of seven adult *Aotus nancymaae* monkeys were selected from the Naval Medical Center Detachment (NMRCD) colony. No monkeys possessed anti-dengue antibody at baseline as determined by enzyme-linked immunoassay (EIA). All procedures were conducted in accordance with protocols approved by the NMRCD Institutional Animal Care and Use Committee. Vaccinated monkeys received vaccine candidate (10 ng) on days 0, 14, and 28 with 10% aluminum hydroxide adjuvant and PBS. The agent was given as 5 divided doses intradermally at the base of the back under anesthesia by trained veterinary staff. Control monkeys received equivalent doses of adjuvant and PBS on days 0, 14, and 28.

Measurement of IgG and IgM

Blood samples were obtained under anesthesia on days 0, 14, 28, and 62. Capture EIAs were standardized and performed in order to detect anti-DENV-1 IgM and IgG in both groups. For IgG and IgM EIAs, 0.10 OD was determined as the cut-off value for positive antibody. Adjusted optical density (OD) values were determined by the difference of the OD of the control antigen-coated well subtracted from the corresponding viral antigen-coated well.

Neutralization Tests

Plaque reduction neutralization test (PRNT) assays were performed using BHK-21 cells. Serial dilutions (1/40, 1/80, 1/160 and 1/640) of heat-inactivated mouse serum were prepared and mixed with an equal volume of a working dilution of DENV-1 West Pac 74 (10-20 PFU/50 μL) and then incubated at 4° C. overnight. At the end of incubation, the diluted mixture was inoculated into 24-well plates containing 3×105 PFU/ml of a BHK cell suspension. After preparation and 7 days of incubation at 37° C., the plaques were counted and 50% plaque reduction was determined by Probit analysis.

Viral Challenge

On day 132, both groups of monkeys were injected with 1 ml of 1.1×104 PFU/ml of DENV-1 West Pac 74 virus as challenge. Physical examinations and blood sampling were performed on days 133, 142, 146, and 160. Anti-DENV-1 IgM and IgG were measured to determine response to primary infection or amnestic response in both groups. On days 133-142 sera were for DENV1 by vero cell culture isolation.

Results

Results of the challenge study are shown in table 2. When administered intradermally to *Aotus nancymaae* monkeys, AMT-inactivated DENV-1 was immunogenic at 14, 28, and 62 days, with detectable IgM and IgG by EIA and with neutralizing antibodies as assessed by 50% plaque reduction neutralization (PRNT50).

Discussion and Conclusions

In this study, psoralen-inactivated dengue-1 viruses are immunogenic in a non-human primate model. There are multiple candidate vaccines in development for dengue virus infections, including DNA vaccines, live attenuated viruses, chimeric vaccines based on an attenuated yellow fever virus, and recombinant subunit vaccines. An inactivated virus vac-

TABLE 2

PRNT and EIA results of DENV-1 of challenge study using psoralen inactivated virus vaccine candidate.

| | | Day 0 | | | Day 14 | | | Day 28 | | | Day 62 | | |
|---|---|---|---|---|---|---|---|---|---|---|---|---|---|
| Group # | Monkey # | DEN EIA IgM | DEN EIA IgG | DEN-1 $PRNT_{50}$ | DEN EIA IgM | DEN EIA IgG | DEN-1 $PRNT_{50}$ | DEN EIA IgM | DEN EIA IgG | DEN-1 $PRNT_{50}$ | DEN EIA IgM | DEN EIA IgG | DEN-1 $PRNT_{50}$ |
| A | 1 | — | — | — | — | — | — | — | — | — | — | — | — |
|   | 2 | — | — | — | — | — | — | — | — | — | — | — | — |
|   | 3 | — | — | — | — | — | — | — | — | — | — | — | — |
|   | 4 | — | — | — | — | — | — | — | — | — | — | — | — |
|   | 5 | — | — | — | — | — | — | — | — | — | — | — | — |
|   | 6 | — | — | — | — | — | — | — | — | — | — | — | — |
|   | 7 | — | — | — | — | — | — | — | — | — | — | — | — |
| B | 8 | — | — | — | 0.323 | 0.297 | — | 0.192 | 1.136 | >=1:640 | — | 1.929 | >=1:640 |
|   | 9 | — | — | — | — | 0.692 | — | — | 0.732 | 1:47 | — | 1.698 | 1:68 |
|   | 10 | — | — | — | 0.429 | 0.439 | — | 0.333 | 1.08 | 1:177 | 0.107 | 1.752 | 1:125 |
|   | 11 | — | — | — | — | — | — | — | 0.349 | 1:81 | — | 1.047 | 1:51 |
|   | 12 | — | — | — | 0.665 | 0.981 | — | 0.231 | 0.985 | 1:184 | — | 1.983 | 1:300 |
|   | 13 | — | — | — | 0.389 | 0.779 | — | 0.161 | 0.908 | 1:48 | — | 1.155 | 1:41 |
|   | 14 | — | — | — | 0.184 | 0.677 | — | 0.262 | 0.787 | 1:201 | — | 1.892 | 1:171 |

"—" indicates EIA or PRNT measurement below threshold
(OD < 0.10 for EIA, PRNT <1:40)
Group A - Control animals (10% Alhydrogel + PBS)
Group B - Vaccinated animals (10 ng inactivated DENV-1 + 10% Alhydrogel + PBS)

Following experimental challenge with DENV-1, vaccinated monkeys showed an amnestic response to infection with a rapid increase in IgG titers. Control monkey, by comparison, showed an increase in IgM without detectable IgG until day 10 after challenge. Control animals demonstrated an average of 3.66 days of viremia post challenge, while vaccinated animals only demonstrated 0.71 days for an 81% reduction of days of viremia in vaccinated vs. control animals (table 3).

TABLE 3

Dengue-1 Virus Challenge Viremia

| Monkey ID | Inoculum | Challenge day | | | | | | | | | | |
|---|---|---|---|---|---|---|---|---|---|---|---|---|
| | | 0 | 1 | 2 | 3 | 4 | 5 | 6 | 7 | 8 | 9 | 10 |
| 1 | SC Control | − | + | − | + | + | − | + | − | − | − | − |
| 2 | SC Control | − | + | + | + | − | + | + | + | − | + | − |
| 3 | SC Control | − | − | − | − | − | − | − | − | − | − | − |
| 4 | SC Control | − | + | + | + | + | − | − | − | − | − | − |
| 5 | SC Control | − | − | + | + | + | + | + | + | − | − | − |
| 6 | SC Control | − | − | + | − | − | − | − | − | − | − | − |
| | | Group Average Viremia: | | | | | | | | | | |
| 7 | SC Vaccine | − | − | − | − | − | − | − | − | − | − | − |
| 8 | SC Vaccine | − | − | − | − | − | − | − | − | − | − | − |
| 9 | SC Vaccine | − | − | − | − | − | − | − | − | − | − | − |
| 10 | SC Vaccine | − | − | + | − | − | − | − | − | − | − | − |
| 11 | SC Vaccine | − | − | − | − | − | − | − | − | − | − | − |
| 12 | SC Vaccine | − | − | − | + | + | − | − | − | − | − | − |
| 13 | SC Vaccine | − | − | + | − | + | − | − | − | − | − | − |

Group Average Viremia:
* Viremia was assayed by IFA on VERO cell culture with monkey sera inoculated.
−, Virus negative
+, Virus detected cine generally will not induce cell-mediated immunity, but experimental data suggests that antibodies and other humoral factors may play a more important role than cell-mediated factors in the prevention of dengue infections. Psoralen inactivation has the potential advantage of being relatively inexpensive and could serve as a boosting component of a prime-boost dengue vaccine strategy.

In conclusion, AMT-inactivated DENV-1 is immunogenic in *Aotus nancymaae* monkeys. Monkeys receiving AMT-inactivated DENV-1 further demonstrate an amnestic response to subsequent live DENV-1 challenge and protected immunized animals against DENV1 infection.

PROPHETIC EXAMPLE 4

Immunogenicity of Psoralen-Inactivated Dengue-2,3,4 Virus Vaccine Candidate

In order to determine the optimal inactivation conditions for selected DENV-2, 3, and 4 virus strains using similar procedure as in example 1. Perform In vitro viral inactivation using mouse sera similar to example 2, and in vivo immunogenicity testing of psoralen-inactivated dengue-1 virus vaccine candidate in *Aotus nancymaae* monkeys as in example 3.

EXAMPLE 5

AMT Photo-Inactivation of Arboviruses Other than Dengue

To extend the use of AMT photo-inactivation to other viruses for the use as vaccines, Yellow Fever (YF), West Nile Virus (WNV), Saint Louis Encephalitis (SLE) and Venezu elan Equine Encephalitis (VEE) viruses were photo-inactivated with AMT and UVA. The virus used are:

1. YF (FMD 1240) C3/36 p-3 Jan. 23, 2008 TITER=5.4× $10^5$ PFU/ml (BHK-21 Sep. 21, 2009 [day 6])
2. WNV (CDC) M29539 (NY99-35262-11) Vero-3 Sep. 17, 2008; TITER=3.07×$10^5$ PFU/ml (LLCMK2 [day 4])
3. SLE TBH-28 CDC M29777 SMB Vero-3 Sep. 17, 2008; TITER=6.8×$10^4$ PFU/ml (BHK-21 Sep. 18, 2009 [day 3])
4. VEE TC 83 TVB 5215 Vero-4 Aug. 26, 2009 TITER=5.45×$10^9$ PFU/ml (VERO-71 [day 2])

Viruses were exposed to increasing doses of UVA alone. The viruses were not inactivated by UVA exposure as demonstrated by the lack of titer reduction with exposure to UVA (table 4).

TABLE 4

Exposure of Arboviruses to UVA (expressed as PFU/ml)

| UVA exp. (minutes) | YF (FMD 1240) | WNV (CDC) M29539 (NY99-35262-11) | SLE TBH-28 CDC M29777 | VEE TC 83 TVB 5215 |
|---|---|---|---|---|
| 0 | 1.47E+05 | 1.00E+05 | 1.10E+04 | 1.80E+08 |
| 1 | 2.40E+05 | 1.10E+05 | 1.10E+04 | 1.55E+08 |
| 5 | 2.20E+05 | 1.00E+05 | 1.10E+04 | 1.30E+08 |
| 10 | 1.50E+05 | 1.70E+05 | 1.30E+04 | 1.80E+08 |
| 20 | 2.00E+05 | 1.60E+05 | 1.10E+04 | 1.23E+08 |

Arboviruses were irradiated with 200 mW/cm2 of UVA at different times (minutes). The viruses were purified with centricep columns and the resultant titers are expressed in PFU/ml.

The viruses were then exposed to AMT and UVA. The viruses used are

1. YF (FMD 1240) C3/36 p-3 Jan. 23, 2008 TITER=5.4× $10^5$ PFU/ml (BHK-21 Sep. 21, 2009 [day 6])
2. WNV (CDC) M29539 (NY99-35262-11) Vero-3 Sep. 17, 2008; TITER=3.07×$10^5$ PFU/ml (LLCMK2 [day 4])
3. SLE TBH-28 CDC M29777 SMB Vero-3 Sep. 17, 2008; TITER=6.8×$10^4$ PFU/ml (BHK-21 Sep. 18, 2009 [day 3])
4. VEE TC 83 TVB 5215 Vero-4 Aug. 26, 2009 TITER=5.45×$10^9$ PFU/ml (VERO-71 [day 2])

With the addition of AMT, the viruses showed a UVA dose dependent inactivation response (table 5). The inactivation conditions mirror those of Dengue Virus AMT UVA inactivation. The in vitro inactivation of Arboviruses suggests that the AMT UVA inactivation method may be used in the production of other potential virus vaccines.

TABLE 5

AMT PHOTO-INACTIVATION OF ARBOVIRUS

| UV-A exp. (minutes) | YF (FMD 1240) | WNV (CDC) M29539 (NY99-35262-11) | SLE TBH-28 CDC M29777 | VEE TC 83 TVB 5215 |
|---|---|---|---|---|
| 0 | 1.47E+05 | 8.00E+04 | 3.20E+03 | 1.72E+09 |
| 1 | 3.68E+04 | 1.68E+04 | 8.00E+01 | 1.60E+08 |
| 5 | 9.00E+01 | 5.00E+01 | 0 | 4.80E+04 |
| 10 | 0 | 0 | 0 | 1.50E+02 |
| 20 | 0 | 0 | 0 | 0 |
| Virus stock | 2.82E+05 | 3.07E+05 | 1.28E+04 | 5.45E+09 |

Photochemical inactivation of Arboviruses with 200 mW/cm2 of UV-A with 10 ug/ml of 4'-Aminomethyltrioxsalen hydrochloride (AMT), at different times (minutes). The viruses were purified with centricep columns after inactivation and the resultant titers are expressed in PFU/ml.

REFERENCES

1. Stephenson J R, 2005. Understanding dengue pathogenesis: implications for vaccine design. Bull World Health Organ 83: 308-14.
2. Wills B A, Nguyen M D, Ha T L, Dong T H, Tran T N, Le T T, Tran V D, Nguyen T H, Nguyen V C, Stepniewska K, White N J, Farrar J J, 2005. Comparison of three fluid solutions for resuscitation in dengue shock syndrome. N Engl J Med 353: 877-89.
3. Panpanich R, Somchai P, Kanjanaratanakom K, 2006. Corticosteroids for treating dengue shock syndrome. Cochrane Database Syst Rev 3: CD003488.
4. Dimaano E M, Saito M, Honda S, Miranda E A, Alonzo M T, Valerio M D, Mapua C A, Inoue S, Kumaori A, Matias R, Natividad F F, Oishi K, 2007. Lack of efficacy of high-dose intravenous immunoglobulin treatment of severe thrombocytopenia in patients with secondary dengue virus infection. Am J Trop Med Hyg 77: 1135-8.
5. Green S, Rothman A, 2006. Immunopathological mechanisms in dengue and dengue hemorrhagic fever. Curr Opin Infect Dis 19: 429-36.
6. Halstead S B, 2003. Neutralization and antibody-dependent enhancement of dengue viruses. Adv Virus Res 60: 421-67.
7. Pang T, Cardosa M J, Guzman M G, 2007. Of cascades and perfect storms: the immunopathogenesis of dengue haemorrhagic fever-dengue shock syndrome (DHF/DSS). Immunol Cell Biol 85: 43-5.
8. Whitehead S S, Blaney J E, Durbin A P, Murphy B R, 2007. Prospects for a dengue virus vaccine. Nat Rev Microbiol 5: 518-28.
9. Durbin A P, McArthur J, Marron J A, Blaney J E, Jr., Thumar B, Wanionek K, Murphy B R, Whitehead S S, 2006. The live attenuated dengue serotype 1 vaccine rDEN1Delta30 is safe and highly immunogenic in healthy adult volunteers. Hum Vaccin 2: 167-73.
10. Guirakhoo F, Kitchener S, Morrison D, Forrat R, McCarthy K, Nichols R, Yoksan S, Duan X, Ermak T H, Kanesa-Thasan N, Bedford P, Lang J, Quentin-Millet M J, Monath T P, 2006. Live attenuated chimeric yellow fever dengue type 2 (ChimeriVax-DEN2) vaccine: Phase I clinical trial for safety and immunogenicity: effect of yellow fever pre-immunity in induction of cross neutralizing antibody responses to all 4 dengue serotypes. Hum Vaccin 2: 60-7.
11. Sun W, Cunningham D, Wasserman S S, Perry J, Putnak J R, Eckels K H, Vaughn D W, Thomas S J, Kanesa-Thasan N, Innis B L, Edelman R, 2008. Phase 2 clinical trial of three formulations of tetravalent live-attenuated dengue vaccine in flavivirus-naive adults. Hum Vaccin 4.
12. Kitchener S, Nissen M, Nasveld P, Forrat R, Yoksan S, Lang J, Saluzzo J F, 2006. Immunogenicity and safety of two live-attenuated tetravalent dengue vaccine formulations in healthy Australian adults. Vaccine 24: 1238-41.
13. Groene W S, Shaw R D, 1992. Psoralen preparation of antigenically intact noninfectious rotavirus particles. J Virol Methods 38: 93-102.
14. Allain J P, Hsu J, Pranmeth M, Hanson D, Stassinopoulos A, Fischetti L, Corash L, Lin L, 2006. Quantification of viral inactivation by photochemical treatment with amotosalen and UV A light, using a novel polymerase chain reaction inhibition method with preamplification. J Infect Dis 194: 1737-44.
15. Lin L, Cook D N, Wiesehahn G P, Alfonso R, Behrman B, Cimino G D, Corten L, Damonte P B, Dikeman R, Dupuis K, Fang Y M, Hanson C V, Hearst J E, Lin C Y, Londe H F, Metchette K, Nerio A T, Pu J T, Reames A A, Rheinschmidt 15. M, Tessman J, Isaacs S T, Wollowitz S, Corash L, 1997. Photochemical inactivation of viruses and bacteria in platelet concentrates by use of a novel psoralen and long-wavelength ultraviolet light. Transfusion 37: 423-35.
16. Berg M, Ros A M, 1994. Treatment of psoriasis with psoralens and ultraviolet A. A double-blind comparison of 8-methoxypsoralen and 5-methoxypsoralen. Photodermatol Photoimmunol Photomed 10: 217-20.
17. Snyder E L, Dodd R Y, 2001. Reducing the risk of blood transfusion. Hematology Am Soc Hematol Educ Program: 433-42.
18. McNeal M M, Rae M N, Ward R L, 1999. Effects of different adjuvants on rotavirus antibody responses and protection in mice following intramuscular immunization with inactivated rotavirus. Vaccine 17: 1573-80.
19. Tang J, Murtadha M, Schnell M, Eisenlohr L C, Hooper J, Flomenberg P, 2006. Human T-cell responses to vaccinia virus envelope proteins. J Virol 80: 10010-20.
20. Sutjipto S, Pedersen N C, Miller C J, Gardner M B, Hanson C V, Gettie A, Jennings M, Higgins J, Marx P A, 1990. Inactivated simian immunodeficiency virus vaccine failed to protect rhesus macaques from intravenous or genital mucosal infection but delayed disease in intravenously exposed animals. J Virol 64: 2290-7.
21. Raviprakash K, Porter K R, Kochel T J, Ewing D, Simmons M, Phillips I, Murphy G S, Weiss W R, Hayes C G, 2000. Dengue virus type 1 DNA vaccine induces protective immune responses in rhesus macaques. J Gen Virol 81: 1659-67.
22. Puri B, Nelson W M, Henchal E A, Hoke C H, Eckels K H, Dubois D R, Porter K R, Hayes C G, 1997. Molecular analysis of dengue virus attenuation after serial passage in primary dog kidney cells. J Gen Virol 78 (Pt 9): 2287-91.
23. Morens D M, Halstead S B, Repik P M, Putvatana R, Raybourne N, 1985. Simplified plaque reduction neutralization assay for dengue viruses by semimicro methods in BHK-21 cells: comparison of the BHK suspension test with standard plaque reduction neutralization. J Clin Microbiol 22: 250-4.
24. Hanson C V, Riggs J L, Lennette E H, 1978. Photochemical inactivation of DNA and RNA viruses by psoralen derivatives. J Gen Virol 40: 345-58.
25. Hearst J E, 1981. Psoralen photochemistry and nucleic acid structure. J Invest Dermatol 77: 39-44.
26. Singh Y, Sawyer L S, Pinkoski L S, Dupuis K W, Hsu J C, Lin L, Corash L, 2006. Photochemical treatment of plasma with amotosalen and long-wavelength ultraviolet light inactivates pathogens while retaining coagulation function. Transfusion 46: 1168-77.
27. Nataraj A J, Black H S, Ananthaswamy H N, 1996. Signature p53 mutation at DNA cross-linking sites in 8-methoxypsoralen and ultraviolet A (PUVA)-induced murine skin cancers. Proc Natl Acadi Sci USA 93: 7961-5.
28. Rassner G, Steinert M, Bercher M, Rodermund O E, Henning D, Mey T, Heinzel M, 1987. [Chronic systemic toxicity of oral photochemotherapy using 8-methoxypsoralen and UVA]. Hautarzt 38: 10-7.
29. Maier H, Schemper M, Ortel B, Binder M, Tanew A, Honigsmann H, 1996. Skin tumors in photochemotherapy for psoriasis: a single-center follow-up of 496 patients. Dermatology 193: 185-91.
30. Mongkolsapaya J, Duangchinda T, Dejnirattisai W, Vasanawathana S, Aviruman P, Jairungsri A, Khemnu N, Tangthawornchaikul N, Chotiyarnwong P, Sae-Jang K, Koch M, Jones Y, McMichael A, Xu X, Malasit P, Screaton G, 2006. T cell responses in dengue hemorrhagic fever: are cross-reactive T cells suboptimal? J Immunol 176: 3821-9.
31. Kyle J L, Balsitis S J, Zhang L, Beatty P R, Harris E, 2008. Antibodies play a greater role than immune cells in heterologous protection against secondary dengue virus infection in a mouse model. Virology.
32. Kliks S C, Nisalak A, Brandt W E, Wahl L, Burke D S, 1989. Antibody-dependent enhancement of dengue virus growth in human monocytes as a risk factor for dengue hemorrhagic fever. Am J Trop Med Hyg 40: 444-51.
33. Boonnak K, Slike B M, Burgess T H, Mason R M, Wu S J, Sun P, Porter K, Rudiman I F, Yuwono D, Puthavathana P, Marovich M A, 2008. Role of dendritic cells in antibody-dependent enhancement of dengue virus infection. J Virol 82: 3939-51.
34. Atrasheuskaya A, Petzelbauer P, Fredeking T M, Ignatyev G, 2003. Anti-TNF antibody treatment reduces mortality in experimental dengue virus infection. FEMS Immunol Med Microbiol 35: 33-42.
35. Dong T, Moran E, Vinh Chau N, Simmons C, Luhn K, Peng Y, Wills B, Phuong Dung N, Thi Thu Thao L, Hien T T, McMichael A, Farrar J, Rowland-Jones S, 2007. High pro-inflammatory cytokine secretion and loss of high avidity cross-reactive cytotoxic T-cells during the course of secondary dengue virus infection. PLoS ONE 2: e1192.
36. Kliks S C, Nimmanitya S, Nisalak A, Burke D S, 1988. Evidence that maternal dengue antibodies are important in the development of dengue hemorrhagic fever in infants. Am J Trop Med Hyg 38: 411-9.
37. Hanson (1983) in: Medical Virology II, de la Maza and Peterson, eds., Elsevier Biomedical, New York, pp. 45-79.

What is claimed is:

1. A method for inactivating a live virus for use as an immunogenic composition comprising:
    a) exposing said virus to an inactivating psoralen, wherein said psoralen is selected from the group consisting of 4'-Aminomethyltrioxalen hydrochloride (AMT), 8-Methoxypsoralen (8-MOP), 4, 5', 8-Trimethylpsoralen (TMP) and a combination thereof, and
    b) exposing said virus to a preselected intensity of an ultraviolet radiation for 5 to 30 minutes, which is sufficiently long to render the virus non-infectious but would not result in degradation of its antigenicity.
2. The method of claim 1, wherein said virus is an Arbovirus.
3. The method of claim 2, wherein said virus is a dengue virus.
4. The method of claim 3, wherein said dengue virus is selected from serotype consisting: dengue-1, dengue-2, dengue-3, dengue-4, and a combination thereof.
5. The method of claim 1, wherein said inactivating psoralen is added to a medium containing said live virus.
6. The method of claim 5, wherein said psoralen is introduced to said medium in 1-4 additions.
7. The method of claim 5, wherein said medium is an inactivation medium or a cell culture medium in which the virus is grown.
8. The method of claim 5, wherein said psoralen is added to the medium at a concentration of 1-100 µg/ml.
9. The method of claim 8, wherein the concentration of said psoralen is 5-25 µg/ml.
10. The method as in claim 1, wherein said ultraviolet radiation exposure is 5 to 10 minutes.
11. The method of claim 1, wherein the intensity of ultraviolet radiation is 150 $\mu W/cm^2$ to 200 $mW/cm^2$.
12. The method of claim 11, wherein the intensity of ultraviolet radiation is 150 $\mu W/cm^2$ to 1500 $\mu W/cm^2$.
13. The method of claim 3, wherein said dengue virus is diluted to a concentration of $1 \times 10^5$ to $1 \times 10^6$ pfu/ml.

14. The method of claim 13, wherein said dengue virus is diluted to a concentration of $3 \times 10^5$ to $5 \times 10^6$ pfu/ml.

15. The method of claim 5, wherein temperature of said medium is maintained below 25 ° C. during said ultraviolet irradiation exposure.

* * * * *